United States Patent [19]

Nassry et al.

[11] Patent Number: 5,415,793
[45] Date of Patent: May 16, 1995

[54] LUBRICANT ADDITIVE TO PREVENT CAMSHAFT AND VALVE TRAIN WEAR IN HIGH PERFORMANCE TURBOCHARGED ENGINES

[75] Inventors: Assadullah Nassry, Warrington, Pa.; Mary A. Dahlstrom, Hopewell Junction, N.Y.; Predrag Panic, Ghent; Mieke Mortier, Ruiselede, both of Belgium

[73] Assignee: Texaco Inc., White Plains, N.Y.

[21] Appl. No.: 214,993

[22] Filed: Mar. 21, 1994

Related U.S. Application Data

[63] Continuation of Ser. No. 872,213, Apr. 22, 1992, abandoned.

[51] Int. Cl.⁶ .......................................... C10M 137/04
[52] U.S. Cl. ................................ 252/32.5; 252/32.7 E
[58] Field of Search ........................................ 252/32.5

[56] References Cited

U.S. PATENT DOCUMENTS

| | | | |
|---|---|---|---|
| 3,004,056 | 10/1961 | Nunn, Jr. et al. | 252/174.16 |
| 3,004,057 | 10/1961 | Nunn, Jr. | 252/174.16 |
| 3,310,489 | 3/1967 | Davis | 252/32.5 |
| 3,547,820 | 12/1970 | Woodward et al. | 252/32.5 |
| 3,567,636 | 3/1971 | Katzenstein | 252/32.5 |
| 4,342,658 | 8/1982 | Tincher et al. | 252/32.5 |
| 4,526,697 | 7/1985 | Cox | 252/32.5 |

OTHER PUBLICATIONS

Smalheer et al., Lubricant Additives, pp. 1–11, 1967.

*Primary Examiner*—Ellen M. McAvoy
*Attorney, Agent, or Firm*—Henry H. Gibson

[57] ABSTRACT

A lubricating oil composition for high-performance gasoline and diesel engines comprising:

(a) a major amount of a base oil having a lubricant viscosity;

(b) a zinc dithiophosphate antiwear/antioxidant additive; and (c) a minor amount of an organic phosphate-ester as antiwear extreme wear additive.

14 Claims, No Drawings

LUBRICANT ADDITIVE TO PREVENT CAMSHAFT AND VALVE TRAIN WEAR IN HIGH PERFORMANCE TURBOCHARGED ENGINES

This application is a continuation of application Ser. No. 07/872,213, filed Apr. 22, 1992, now abandoned.

BACKGROUND OF THE INVENTION

This invention relates to lubricating oil compositions and more particularly to a lubricating oil composition for hi-performance gasoline and diesel engines.

The conventional zinc dithiophosphates used as antiwear lubricants in engine oils do not provide adequate camshaft and valve train wear protection on exposure to severe environment of modern high performance turbocharged engines.

One of the problems involved in the engines is the wear on moving parts. The highest source of engine wear is generally valve train wear (VTW). This is particularly true on engines which have sliding contact between the camshaft lobes and the lifters or followers. Engine oil additives, particularly antiwear additives, are the primary source of preventing excessive VTW. There are many different engine valve train designs and metallurgies in use, which have somewhat different wear characteristics. Also, wear is affected by engine operating condition. Many VTW tests use higher-than-normal valve spring loads and/or special metallurgy wear parts to achieve good wear discrimination in a reasonable length test.

As a result, there are many different VTW tests in use. There are standard VTW tests which provide the wear protection requirements for engine oil performance categories. In addition, some engine manufacturers have their own VTW tests which they require before they approve an oil for use in their engines. Most VTW tests are difficult enough that engine oils must be carefully formulated to achieve both sufficient wear protection and economical additive cost.

Thus, of the present invention is to provide a lubricant additive which will prevent wear in moving parts in a high performance turbocharged engine, including the camshaft and valve train of such engines.

DISCLOSURE STATEMENT

U.S. Pat. Nos. 3,004,056 and 3,004,057 disclose a method of producing surface active compositions containing mixtures of primary and secondary phosphate esters of hydroxylic organic compounds.

U.S. Pat. No. 3,547,820 discloses a mineral lubricating oil composition containing about 0.5% to about 25% by weight of a material selected from a phosphate ester and a salt of a phosphate ester of phosphoric acid and an oxyalkylene ether or an organic hydroxy compound. The organic hydroxy compound is selected from alkyl phenols and aliphatic straight chain alcohols, the phosphate ester being selected from monoesters, diesters and mixtures thereof, the oxyalkylene group of the oxyalkylene ether comprising a maximum of about 50% by weight thereof.

U.S. Pat. No. 3,933,658 discloses a metalworking composition and an additive for a metalworking composition which imparts extreme pressure, antiwear, and corrosion-inhibiting properties to the metalworking composition. The additive comprises a phosphate ester and a sulphur compound. The composition comprises the additive used in an oil-based vehicle.

SUMMARY OF THE INVENTION

This invention provides a lubricating oil composition for high-performance gasoline and diesel engines comprising:

(a) a major amount of a base oil having a lubricant viscosity;

(b) a zinc dithiophosphate antiwear/antioxidant additive; and (c) a minor portion of, as an anti-camshaft/valve train anti-wear additive, organic phosphate esters represented by the formulas

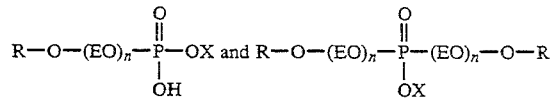

wherein EO is ethylene oxide; R is a branched or linear chain ($C_6$–$C_{30}$) alkyl or alkylaryl group; X is selected from the group consisting of a residue of hydrogen, ammonia, an amine, an alkali, an alkaline earth metal; and n is an integer of 1 to 10.

DETAILED DESCRIPTION OF THE INVENTION

The lubricant oil organic phosphate ester additives of this invention may be represented by the following structures:

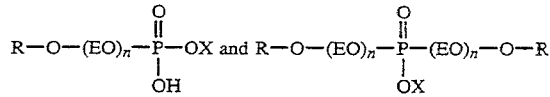

The phosphate esters are mono- and diphosphate ester and mixtures wherein (EO) is ethylene oxide; R is selected from the group consisting of linear or branched chain alkyl or alkylaryl groups having about 6 to about 30 carbon atoms, preferably about 8 to about 20 carbon atoms, wherein the alkylaryl groups have about 6 to about 30 carbon atoms, preferably about 8 to about 18 carbon atoms; X is selected from the group consisting of a residue of hydrogen, ammonia, an amine, an alkali, an alkaline earth metal and a mixture thereof; and n is an integer of 1 to 10. Metals such as lithium, sodium, potassium, rubidium, cesium, calcium, strontium and barium are examples of X.

According to the present invention, it has now been found that incorporation of an organic phosphate ester at 0.05–1.0 wt % levels in engine oils with a conventional additive package and VI Improver provides superior camshaft and valve train wear performance in severe European camshaft and valve train wear tests.

The organic phosphate esters used in the compositions of the present invention are those more fully disclosed in U.S. Pat. Nos. 3,004,056 and 3,004,057 which are incorporated herein by reference.

The phosphate esters utilized are generally obtained by esterifying 1 mole of phosphorus pentoxide with 2 to 4.5 moles of a nonionic surface active agent by condensing at least 1 mole of ethylene oxide with 1 mole of a compound having at least 6 carbon atoms and a reactive hydrogen atom. These nonionic surface active agents are well known in the art and are generally prepared by condensing a polyglycol ether containing a suitable number of alkoxy groups or 1,2-alkylene oxide, or a substituted alkylene oxide such as a substituted propylene oxide, butenyl oxide or preferably ethylene oxide with an organic compound at least 6 carbon atoms and a reactive hydrogen atom. Examples of compounds containing a reactive hydrogen atom are alcohols, phenols, thiols, primary and secondary amines and carboxylic and sulfonic acids and their amides. The amount of alkylene oxide or equivalent condensed with a reactive chain will generally depend upon the particular compound employed.

About 20 to 85% by weight of combined alkylene oxide is generally obtained in a condensation product, however, the optimum amount of ethylene oxide or equivalent utilized will depend upon the desired hydrophobic-lipophilic balance.

Preferably, the nonionic surface active agents utilized are derivatives of alkylated and polyalkylated phenols, multibranched chain primary aliphatic alcohols having the molecular configuration of an alcohol and are produced by the Oxo process from a polyolefin of at least 7 carbon atoms or straight chain aliphatic alcohols of at least 10 carbon atoms.

Examples of suitable nonionic surface active agent condensation products which can be in turn reacted with phosphorus pentoxide to produce the phosphate esters utilized as novel camshaft and valve train antiwear-extreme pressure (EP) lubricants in engine oils of this invention are listed below in Table I.

TABLE I

Octadecanol + 2 moles ethylene oxide
Hexadecanol + 4 moles ethylene oxide
1-Eicosanol + 6 moles ethylene oxide
Lauryl alcohol + 4 moles ethylene oxide
Hexadecanol + 3 moles propylene oxide
Octadecanol + 4 moles propylene oxide
Cetyl alcohol + 2 moles ethylene oxide
1-Octacosanol + 4 moles ethylene oxide
Oleyl alcohol + 2 moles ethylene oxide
Oleyl alcohol + 4 moles ethylene oxide
Tridecyl alcohol + 4 moles ethylene oxide
Dodecyl phenol + 5 moles ethylene oxide
Hexadecyl phenol + 3 moles ethylene oxide
Tri-n-octyl phenol + 4 moles ethylene oxide
Tri-n-octyl phenol + 5 moles propylene oxide
Dodecyl phenol + 3 moles propylene oxide
Dinonyl phenol + 1.5 moles propylene oxide
Diisohexyl phenol + 2 moles propylene oxide
Tri-n-butyl phenol + 3 moles ethylene oxide
Tri-n-butyl phenol + 2 moles propylene oxide
Tri-n-butyl phenol + 4 moles propylene oxide The base oil which is a major amount of the present lubricating oil composition may have a viscosity of 4.0 to 10.0 cSt at 100° C. and preferably the base oil is a solvent refined mineral oil, a polyalphaolefin or a mixture of mineral oils and polyalphaolefins. Also, the base oil may be a single-grade or multigraded oil. In the case it is a multigraded oil it is multigraded with polymeric viscosity index improvers.

While it is known that the phosphate esters of the present invention, as described herein, can contribute to the antiwear-extreme pressure (EP) performance characteristics of a lubricant composition, it has now been found that these lubricants at very low concentrations in engine oils due to a unique effect with zinc dithiophosphate additive, protects camshaft and valve train wear in high performance turbocharged engines. The antiwear-(EP) performance of the present phosphate esters has been demonstrated in various engine wear tests, as discussed below in the Examples.

In order to show effectiveness of the present invention, the following Examples are provided.

EXAMPLE 1

An SAE 20W-50 engine oil (I) was formulated based on 82.80 wt % solvent refined mineral oils, 6.50 wt % VI improver and 10.70 wt % of additive package containing 1.0 wt % zinc dithiophosphate (ZDTP) antiwear lubricant. A similar oil (II) of the same composition was also formulated and fortified with 0.20 wt % of an organic phosphate ester antiwear-EP lubricant. The phosphate ester utilized was produced by the reaction of 1 mole $P_2O_5$ with 2 to 4.5 moles of a condensation product of one mole of oleyl alcohol and 4 moles of ethylene oxide in accordance with the methods disclosed in U.S. Pat. Nos. 3,004,056 and 3,004,057. Both oils were then evaluated in a VW cam and tappet wear test. The data obtained are shown below in Table II.

TABLE II

VW CAM AND TAPPET WEAR TEST

| | Formulation Number | | |
|---|---|---|---|
| | I | II | |
| Test Oil Grade | SAE 20W-50 | SAE 20W-50 | |
| Zinc Dithiophosphate, wt % | 1.00 | 1.00 | |
| Phosphate ester oleyl alcohol + 4 moles E.O. | None | 0.20 | |
| Test Criteria | | | Limits |
| Cam wear, micron: | | | |
| Cam No. 1 | 44 | 48 | 100 Max |
| Cam No. 2 | 54 | 47 | |
| Cam No. 3 | 87 | 74 | |
| Cam No. 4 | 47 | 61 | |
| Tappet wear, micron: | | | |
| Tappet No. 1 | 94 | 74 | 75 Max |
| Tappet No. 2 | 73 | 61 | |
| Tappet No. 3 | 127 | 81 | |
| Tappet No. 4. | 128 | 74 | |
| Tappet No. 5 | 80 | 41 | |
| Tappet No. 6 | 116 | 57 | |
| Tappet No. 7 | 111 | 55 | |
| Tappet No. 8 | 83 | 34 | |

The data reveal noticeably better tappet wear performance for formulation II containing the phosphate ester and the zinc dithiophosphate combination than formulation I, based on zinc dithiophosphate alone. This is attributed to a novel lubricity performance of the long chain alkyl phosphate ester with zinc dithiophosphate.

EXAMPLE 2

An SAE 15W-40 engine oil (I) was formulated based on 79.48 wt % mineral oils, 8.50 wt % VI improver and 12.02 wt % additive package containing 1.20 wt % mixed zinc dithiophosphates (ZDTP) antiwear lubricant. A similar oil (II) of the same composition was also formulated and fortified with 0.05 wt % of the same alkyl phosphate ester utilized in Example 1. Both oils were then evaluated for wear performance in a Peugeot TU3 valve train wear test. The data obtained are shown below in Table III.

TABLE III
PEUGEOT TU3 VALVE TRAIN WEAR TEST

| | Formulation Number | | |
|---|---|---|---|
| | I | II | |
| | Test Oil Grade | | |
| | SAE 15W-40 | SAE 15W-40 | |
| Mixed Zinc Dithiophosphates, wt % | 1.20 | 1.20 | |
| Phosphate Ester Oleyl Alcohol + 4 moles E. O. | None | 0.05 | |
| Test Criteria | | | Limits |
| Average Rocker Pad Merit | 7.69 | 9.43 | 7.50 min |
| Average Cam Wear, Micron | 6.50 | 3.70 | 15.0 max |
| Maximum Cam Wear, Micron | 12.00 | 5.00 | 20.0 max |

The above data clearly show better rocker pad merit rating as well as superior cam wear performance for formulation II containing the mixed zinc dithiophates and alkyl phosphate ester combinations than formulation I, based on mixed zinc dithiophosphates alone. This is another demonstration of a novel lubricity performance of alkyl phosphate ester with mixed zinc dithiophosphates.

EXAMPLE 3

An SAE 15W-40 engine oil (IB) was formulated based on 79.48 wt % solvent refined mineral oils, 8.50 wt % VI improver and 12.02 wt % additive package containing 1.20 wt % mixed zinc dithiophosphates (ZDTP) antiwear lubricant. A similar oil (IIB) of the same composition was also formulated and fortified with 0.10 wt % of the same alkyl phosphate ester used in Example 1. Two SAE 10W oils (IA/IIA) were also formulated with solvent refined mineral oils without VI improver based on the stated treat level of additive package, with and without 0.10 wt % of the alkyl phosphate ester. All four oils were then evaluated in Part A and Part B of the Mercedes-Benz OM 616 Kombi test for valve train wear, cylinder wear and ring sticking. The data obtained are shown below in Table IV.

TABLE IV
MERCEDES BENZ OM 616 KOMBI TEST

| | Formulation Number | | |
|---|---|---|---|
| | I | II | |
| | Test Oil Grades | | |
| | SAE 10W (A) SAE 15W-40 (B) | SAE 10W (A) SAE 15W-40 (B) | |
| Mixed Zinc Dithiophosphates, wt % | 1.20 | 1.20 | |
| Phosphate Ester Oleyl Alcohol + 4 moles E. O. | None | 0.10 | |
| Test Criteria | | | Limits |
| Cam wear, avg, micron/1000 km | 0.70 | 0.50 | 0.50 avg |
| Cam wear, max, micron/1000 km | 1.40 | 1.10 | 1.00 max |
| Cylinder wear, avg, micron/1000 km | 0.30 | 0.20 | 0.50 avg |
| Cylinder wear, max, micron/1000 km | 1.30 | 0.60 | 1.20 max |

The data obtained above, show better cam and cylinder wear performance for formulation II, containing the mixed zinc dithiophosphates and alkyl phosphate ester combinations than formulation I based on mixed zinc dithiophosphates alone. This is another demonstration of their novel antiwear performance.

EXAMPLE 4

An SAE 15W-40 engine oil (I) was formulated based on 80.05 wt % solvent refined mineral oils, 7.0 wt % VI improver and 12.95 wt % additive package containing 1.20 wt % mixed zinc dithiophosphates antiwear additive. A similar oil (II) of the same composition was also formulated and fortified with 0.05 wt % of the same alkyl phosphate ester stated in Example 1. Both oils were then evaluated for cam lobe wear in the ASTM Sequence VE engine test. The data obtained are shown below in Table V.

TABLE V
ASTM SEQUENCE VE ENGINE TEST

| | Formulation Number | | |
|---|---|---|---|
| | I | II | |
| | Test Oil Grade | | |
| | SAE 15W-40 | SAE 15W-40 | |
| Mixed Zinc Dithiophosphates, wt % | 1.20 | 1.20 | |
| Phosphate Ester Oleyl Alcohol + 4 moles E. O. | None | 0.05 | |
| Test Criteria | | | Limits |
| Cam Lobe Wear, max, mils | 16.40 | 7.50 | 15.0 max |
| Cam Lobe wear, avg, mils | 7.82 | 3.00 | 5.0 max |

Similarly, the data of Table V above, reveals superior cam lobe wear performance for formulation II containing the mixed zinc dithiophosphates and alkyl phosphate ester combination than formulation I based on mixed zinc dithiophosphates alone. This is a further confirmation of the novel antiwear performance of the two additives.

The stated four examples clearly demonstrate the novel antiwear-EP performance of the phosphate ester of oleyl alcohol + 4 moles of ethylene oxide in combinations with zinc dithiophosphates in engine oils to prevent camshaft and valve train wear in modern high performance turbocharger engines.

While this invention has been described with reference to certain specific embodiments, it will be recognized by those skilled in the art that many variations are possible without departing from the scope of the present invention defined in the following claims.

We claim:

1. A turbocharged high performance gasoline and diesel car and truck engine lubricant oil composition consisting essentially of solvent refined mineral oils, a polymeric viscosity index improver and an additive package containing zinc dithiophosphates, and about 0.05 to 0.2 wt % of an organic phosphate ester selected from the group consisting of

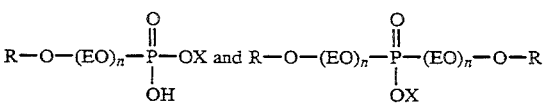

and mixtures thereof; wherein EO is ethylene oxide; R is a linear or branched chain ($C_6$–$C_{30}$) alkyl or alkylaryl group; X is selected from the group consisting of hydrogen, ammonia, an amine, an alkali and an alkaline earth metal; and n is an integer of 1 to 10.

2. A method of preventing camshaft and valve train wear in turbocharged high performance gasoline and diesel car and truck engines comprising adding to said engines an effective amount of a high-performance gasoline and diesel engine lubricating composition according to claim 1.

3. A high-performance gasoline and diesel engine lubricating oil composition comprising:
(a) a major amount of a base oil having a lubricant viscosity;
(b) a zinc dithiophosphate antiwear/antioxidant additive; and
(c) a minor amount of about 0.05 to 0.2 wt % organic phosphate esters antiwear—extreme pressure additives to prevent camshaft and valve train wear, said organic phosphate esters being represented by the following structures:

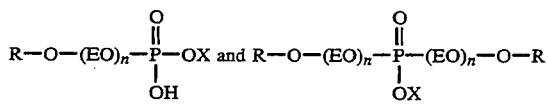

wherein EO is ethylene oxide; R is a branched or linear chain ($C_6$–$C_{30}$) alkyl or alkylaryl group; X is selected from the group consisting of a residue of hydrogen, ammonia, an amine, an alkali metal and an alkaline earth metal; and n is a number from 1 to 10.

4. The lubricating oil composition of claim 3, wherein said base oil has a viscosity of 4.0 to 10.0 cSt at 100° C.

5. The lubricating oil composition of claim 3, wherein said base oil is multigraded with polymeric viscosity index improvers.

6. The lubricating oil composition of claim 3, wherein the base oil is a solvent refined mineral oil, a polyalphaolefin or a mixture of mineral oils and polyalphaolefins.

7. The lubricating oil composition of claim 3, wherein said alkali and alkaline earth metals are selected from the group consisting of lithium, sodium, potassium, rubidium, cesium, calcium, strontium and barium.

8. The lubricating oil composition of claim 3, wherein said organic phosphate ester is a mono-or di-phosphate ester.

9. A method of preventing camshaft and valve train wear in turbocharged high performance gasoline and diesel car and truck engines comprising adding to said engines an effective amount of a high-performance gasoline and diesel engine lubricating composition according to claim 3.

10. A method of preventing camshaft and valve train wear in turbocharged high performance gasoline and diesel car and truck engines comprising adding to said engines an effective amount of a high-performance gasoline and diesel engine lubricating composition according to claim 4.

11. A method of preventing camshaft and valve train wear in turbocharged high performance gasoline and diesel car and truck engines comprising adding to said engines an effective amount of a high-performance gasoline and diesel engine lubricating composition according to claim 5.

12. A method of preventing camshaft and valve train wear in turbocharged high performance gasoline and diesel car and truck engines comprising adding to said engines an effective amount of a high-performance gasoline and diesel engine lubricating composition according to claim 6.

13. A method of preventing camshaft and valve train wear in turbocharged high performance gasoline and diesel car and truck engines comprising adding to said engines an effective amount of a high-performance gasoline and diesel engine lubricating composition according to claim 7.

14. A method of preventing camshaft and valve train wear in turbocharged high performance gasoline and diesel car and truck engines comprising adding to said engines an effective amount of a high-performance gasoline and diesel engine lubricating composition according to claim 8.

* * * * *